United States Patent
Chen et al.

(10) Patent No.: US 11,350,902 B2
(45) Date of Patent: Jun. 7, 2022

(54) OPTICAL BASED SUBJECT MOTION DETECTION IN IMAGING SYSTEMS

(71) Applicants: KONINKLIJKE PHILIPS N.V., Eindhoven (NL); TSINGHUA UNIVERSITY, Beijing (CN); UNIVERSITY OF WASHINGTON, Seattle, WA (US)

(72) Inventors: Huijun Chen, Tsinghua (CN); Jinnan Wang, Seattle, WA (US); Chun Yuan, Bellevue, WA (US)

(73) Assignees: KONINKLIJKE PHILIPS N.V., Eindhoven (NL); TSINGHUA UNIVERSITY, Beijing (CN); UNIVERSITY OF WASHINGTON, Seattle, WA (US)

( * ) Notice: Subject to any disclaimer, the term of this patent is extended or adjusted under 35 U.S.C. 154(b) by 1638 days.

(21) Appl. No.: 15/104,432

(22) PCT Filed: Dec. 4, 2014

(86) PCT No.: PCT/IB2014/066569
§ 371 (c)(1),
(2) Date: Jun. 14, 2016

(87) PCT Pub. No.: WO2015/092593
PCT Pub. Date: Jun. 25, 2015

(65) Prior Publication Data
US 2016/0310093 A1    Oct. 27, 2016

Related U.S. Application Data

(60) Provisional application No. 61/918,770, filed on Dec. 20, 2013.

(51) Int. Cl.
*A61B 6/00* (2006.01)
*A61B 6/03* (2006.01)
(Continued)

(52) U.S. Cl.
CPC .............. *A61B 6/527* (2013.01); *A61B 5/055* (2013.01); *A61B 6/032* (2013.01); *A61B 6/037* (2013.01);
(Continued)

(58) Field of Classification Search
CPC ..... A61B 6/032; A61B 6/0407; A61B 6/0492; A61B 6/527; A61B 6/54; A61B 6/037;
(Continued)

(56) References Cited

U.S. PATENT DOCUMENTS 7,128,714 B1    10/2006 Antonelli
7,372,935 B2    5/2008 Bernhardt
(Continued)

FOREIGN PATENT DOCUMENTS

WO    2000072748    12/2000
WO    2011033422    3/2011

*Primary Examiner* — Bo Joseph Peng
(74) *Attorney, Agent, or Firm* — Larry Liberchuk

(57) ABSTRACT

An imaging system (100) includes a subject support (114) that supports a subject in an examination region (106). The imaging system further includes a detector (112) that detects a signal traversing the examination region, generating an output indicative of the examination region. The imaging system further includes a subject motion sensing system (118) that includes an optical system (206, 208, 214) that detects motion of the subject in the examination region and generates motion data indicative thereof. The imaging system further includes a console (122) that controls at least one of data acquisition or reconstruction based on the motion data.

11 Claims, 9 Drawing Sheets

(51) Int. Cl.
    *A61B 6/04*         (2006.01)
    *A61B 5/055*       (2006.01)
    *A61B 6/02*         (2006.01)

(52) U.S. Cl.
    CPC .......... *A61B 6/0407* (2013.01); *A61B 6/0492* (2013.01); *A61B 6/54* (2013.01); *A61B 6/541* (2013.01); *A61B 6/027* (2013.01); *A61B 6/4035* (2013.01); *A61B 6/5288* (2013.01)

(58) Field of Classification Search
    CPC ....... A61B 6/541; A61B 6/027; A61B 6/4035; A61B 6/5288; A61B 5/055
    See application file for complete search history.

(56) References Cited

U.S. PATENT DOCUMENTS

| | | |
|---|---|---|
| 8,390,291 B2 | 3/2013 | Macfarlane |
| 2004/0116804 A1 | 6/2004 | Mostafavi |
| 2012/0101344 A1 | 4/2012 | Desjardins |
| 2013/0310655 A1 | 11/2013 | Sachs |

OPTICAL BASED SUBJECT MOTION DETECTION IN IMAGING SYSTEMS

CROSS REFERENCE TO RELATED APPLICATIONS

This application is the U.S. National Phase application under 35 U.S.C. § 371 of International Application No. PCT/IB2014/066569, filed Dec. 4, 2014, published as WO 2015/092593 on Jun. 25, 2015, which claims the benefit of U.S. Provisional Patent Application No. 61/918,770 filed Dec. 20, 2013. These applications are hereby incorporated by reference herein.

The following generally relates to imaging and more particularly to detecting subject motion through an optical motion sensing system of an imaging system, and is described with particular application to computed tomography (CT). However, the following is also amenable to other imaging modalities, including positron emission tomography (PET), single photon emission computed tomography (SPECT), a magnetic resonance imaging (MRI), and/or other medical and/or non-medical imaging modalities.

Computed tomography (CT) is a non-invasive imaging procedure. A CT scanner generally includes an x-ray tube mounted on a rotatable gantry opposite a detector array across an examination region. The rotatable gantry and hence the x-ray tube rotate around the examination region and a portion of a subject and/or object therein. The x-ray tube is configured to emit radiation that traverses the examination region and the portion of a subject and/or object in the examination region.

The detector array detects radiation that traverses the examination region and generates projection data indicative of the detected radiation and hence the scanned portion of the subject and/or object. The projection data is reconstructed to generate volumetric image data indicative of the scanned portion of the subject and/or object. The volumetric image data can be processed to generate one or more images indicative of the scanned portion of the subject.

Subject motion, voluntary and involuntary, may introduce motion artifact (e.g., blurring) into the projection data and hence the reconstructed volumetric image data and/or the generated one or more images. An approach to reducing or mitigating motion artifact is to track a motion pattern of the subject and then synchronize (or gate) data acquisition with the tracked motion pattern. The motion pattern is tracked, in one instance, using an external device such as a breathing belt, external coil, etc., or a pre-scan to measure motion.

Unfortunately, external device such as breathing belts, are susceptible to signal drift. With signal drift, error in a measurement will propagate through the subsequent measurements, which will shift the acceptance window such that data is acquired during noisier motion phases, increasing motion artifact in the generated images. Furthermore, external device such as breathing belts may also be inconvenient and uncomfortable for patients.

Aspects described herein address the above-referenced problems and others.

The following describes an approach in which an optical (e.g., structured-light) based non-contact motion tracking/monitoring device, which requires neither external devices affixed to the subject nor pre-acquisitions to accurately measure motion, tracks subject motion in connection with imaging. The tracked motion can be used to gate scanning, temporarily pause scanning if motion should become too high, correct for motion in motion-compensated reconstruction, identify a sub-set of data with predetermined motion characteristic in acquired image data to reconstruct, etc.

In one aspect, an imaging system includes a subject support that supports a subject in an examination region. The imaging system further includes a detector that detects a signal traversing the examination region, generating an output indicative of the examination region. The imaging system further includes a subject motion sensing system that includes an optical system that detects motion of the subject in the examination region and generates motion data indicative thereof. The imaging system further includes a console that controls at least one of data acquisition or reconstruction based on the motion data.

In another aspect, a method includes projecting an optical pattern of a portion of a subject in an examination region of an imaging system. The method further includes detecting a first reflected optical pattern, which is the projected optical pattern reflected off the subject at a first time, and generating a first signal indicative of the first reflected optical pattern. The method further includes detecting a second reflected optical pattern, which is the projected optical pattern reflected off the subject at a second time, and generating a second signal indicative of the second reflected optical pattern. The method further includes determining a difference between the first and the second generated signals, generating a first motion signal. The method further includes controlling at least one of data acquisition or reconstruction based on the first motion signal.

In another aspect, a computer readable storage medium is encoded with computer readable instructions, which, when executed by a processer, causes the processor to: detect subject motion of a subject in an examination region of an imaging system based on an optical system that does not contact the subject.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with a subject motion sensing system.

FIG. 2 schematically illustrates an example of the subject motion sensing system.

Figure 1:
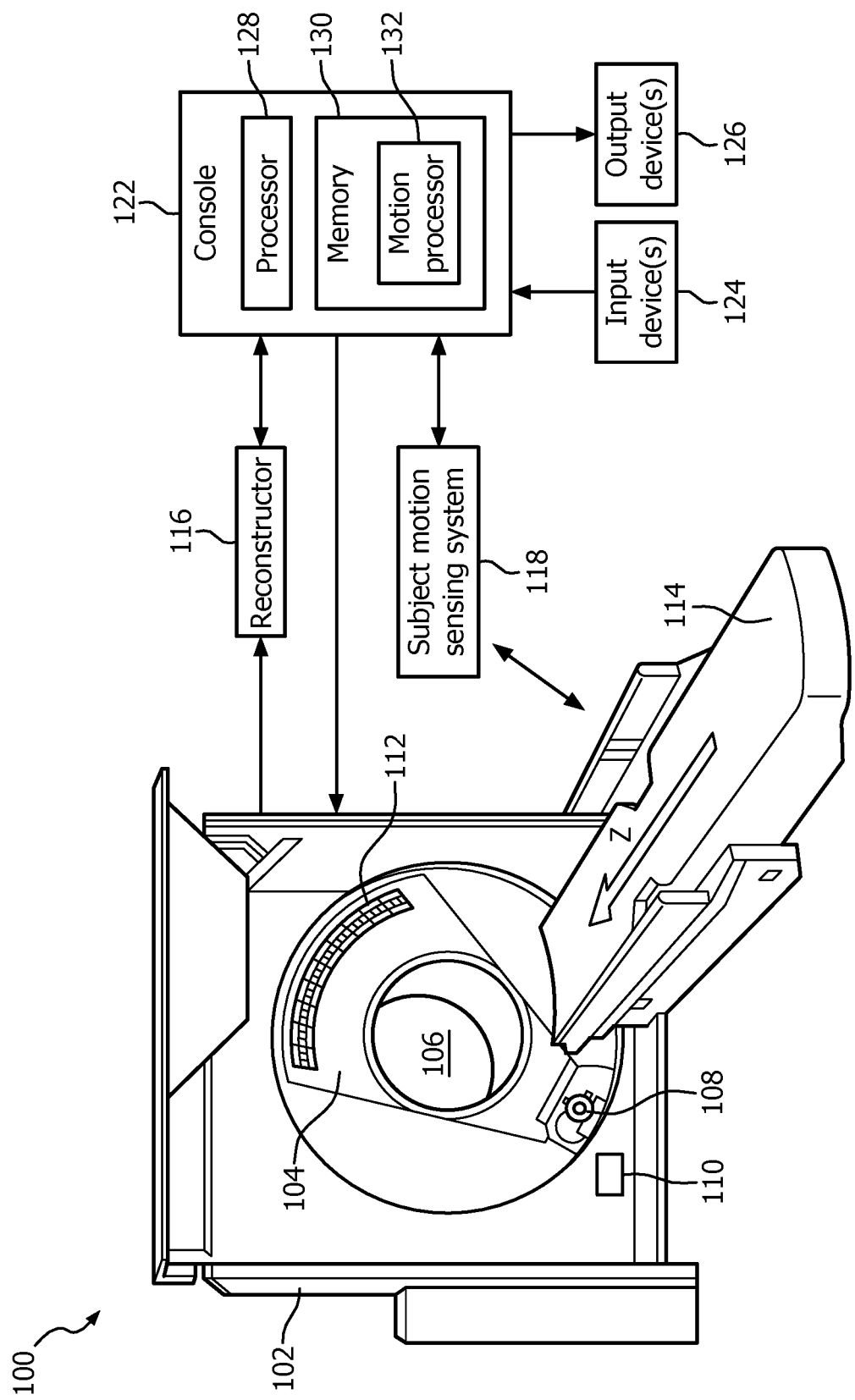

Initially referring to FIG. 1, an imaging system 100 such as a computed tomography (CT) scanner is illustrated. In other embodiments, the imaging system 100 includes as positron emission tomography (PET), single photon emission computed tomography (SPECT), a magnetic resonance imaging (MRI), and/or other scanner.

The illustrated imaging system 100 includes a generally stationary gantry 102 and a rotating gantry 104, which is rotatably supported by the stationary gantry 102 and rotates around an examination region 106 about a z-axis.

A radiation source 108, such as an x-ray tube, is supported by the rotating gantry 104 and rotates with the rotating gantry 104 about the examination region 106, and emits radiation that traverses the examination region 106.

A radiation controller 110 turns radiation emission "on" and "off." For this, the radiation controller 110 can move a filter, which substantially or fully attenuates radiation, in and out of the path of the emitted beam, control a grid voltage of a switching grid, which allows or inhibits electrons to flow from the cathode to the anode of the source, supply and remove a voltage (or power) of the source 108, etc. to turn radiation emission "on" and "off."

A one or two dimensional radiation sensitive detector array 112, located opposite the radiation source 108 across the examination region 106, includes one or more rows of detector pixels arranged along the z-axis. The detector pixels detect radiation traversing the examination region 106 and generate a signal or projection data indicative thereof.

A subject support 114 such as a couch supports a subject in the examination region 106 before, during and/or after scanning the subject.

A reconstructor 116 reconstructs the projection data and generates volumetric image data indicative of the examination region 106. The reconstructor 116 can employ filtered backprojection (FBP), iterative, and/or other reconstruction algorithms, such as a motion-compensated reconstruction algorithm. The reconstructor 116 can also reconstruct only a sub-set of acquired data with subject motion characteristics of interest.

A subject motion sensing system 118 senses initial and subsequent motion states of a subject in the examination region 106 and generates signals indicate thereof. The subject motion sensing system 118 senses a motion state before, during and/or after scanning the subject. Motion at a motion state(s) and/or between motion states may be due to sneezing, coughing, blinking, swallowing, yawning, breathing, cardiac, rolling, moving appendages (e.g., arms, legs, the head, etc.), and/or other voluntary and/or involuntary motion. As described in greater detail below, the subject motion sensing system 118, in one instance, employs optical components to sense the motion states.

The optical components do not physically attach or contact the subject. As such, the inconvenience and discomfort associated with wearable motion sensing devices (e.g., a motion belts and the like) are mitigated. Furthermore, the optical components sense information that can be utilized to determine absolute and/or relative motion of the subject between two motion states (e.g., an initial baseline and a subsequent). As such, signal drift and/or other issues associated with devices that sense relative subject motion are mitigated. Also described below, the optical components can transmit and detect optical signals in the non-visible region of the electromagnetic spectrum. In this case, the subject is unaware of the subject motion sensing system 118.

An operator console 122, such as a computer or computing system, includes an input device 124 such as a keyboard, a mouse, a touchscreen, etc. and an output device 126 such as a monitor or the like. The operator console 122 further includes a computer processor 128 (e.g., a microprocessor, a central processing unit, a controller, etc.) and computer readable storage medium ("memory") 130, which excludes transitory medium and includes physical memory and/or other non-transitory storage medium. The memory 130 stores one or more computer readable instructions (software), which, when executed by the computer processor 128, allows the operator to control one or more components and/or functions of the imaging system 100.

The memory 130 also stores computer readable instructions for a motion processor 132. The motion processor 132 processes the signals from the subject motion sensing system 118. The motion processor 132, based on a result of the processing of the signal, in one instance, generates a scan command signal, which is conveyed to the radiation controller 110. The radiation controller 110, in response to receiving the scan command signal, can gate data acquisition (e.g., turn emission "on" only during a motion phase of interest), turn emission "off" and "on" (e.g., so that the data is acquired only when subject motion satisfies or is below a predetermined motion threshold and the subject is not irradiated when the motion does not satisfy or exceeds the predetermined motion threshold), etc.

In another instance, the motion processor 132 generates a motion signal, which is conveyed to the reconstructor 114 and used by the reconstructor 114 in a motion-compensated reconstruction. In another instance, the motion processor 132 generates a motion signal, which is used to identify a sub-set of the acquired data for the reconstructor 114 to reconstruct. The reconstructor 114 and/or other component can identify the sub-set of the acquired data to reconstruct. For example, the motion signal can be used to identify data acquired when motion was below a predetermined threshold. The identified sub-set of data can be reconstructed, whereas the remaining data is not reconstructed. In these cases, the motion signal can include a numerical value indicating an amount of deformation.

Figure 2:
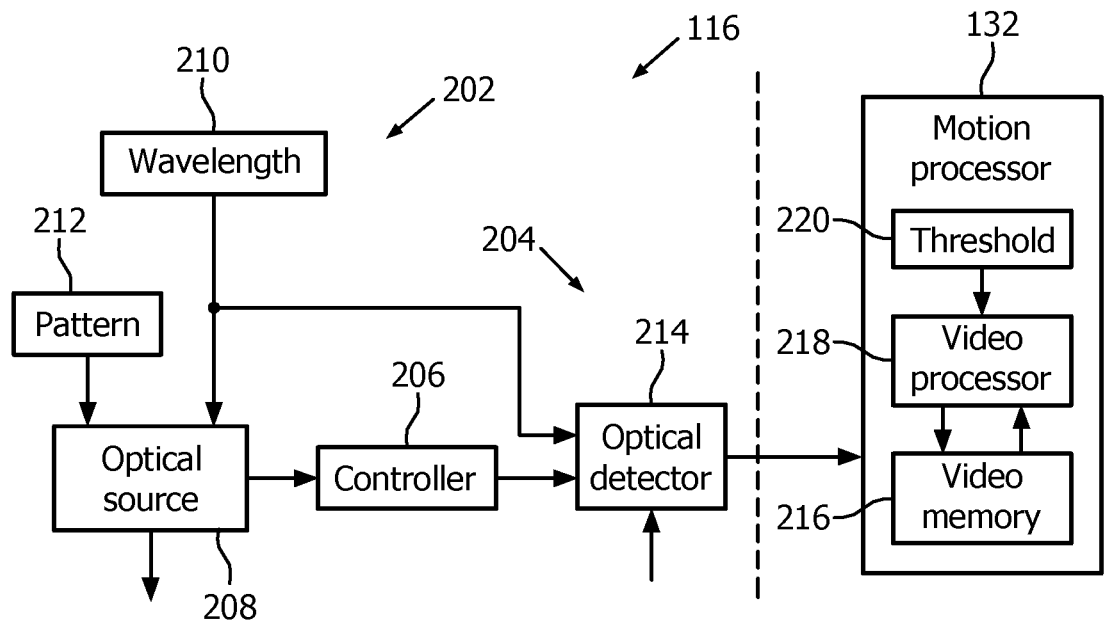

FIG. 2 schematically illustrates an example of the subject motion sensing system 118 and the motion processor 132.

In this example, the subject motion sensing system 118 includes a transmitting portion 202, a receiving portion 204, and a controller 206.

The transmitting portion 202 includes an optical source 208. The optical source 208 generates and transmits/emits an optical signal with a pattern and has a wavelength in one or more of the infrared, the visible light, or the ultraviolet sub-regions of the electromagnetic spectrum. The particular wavelength of the optical signal is determined, for example, based on a pre-determined, but configurable, wavelength 210 range setting.

Figures 3, 4:
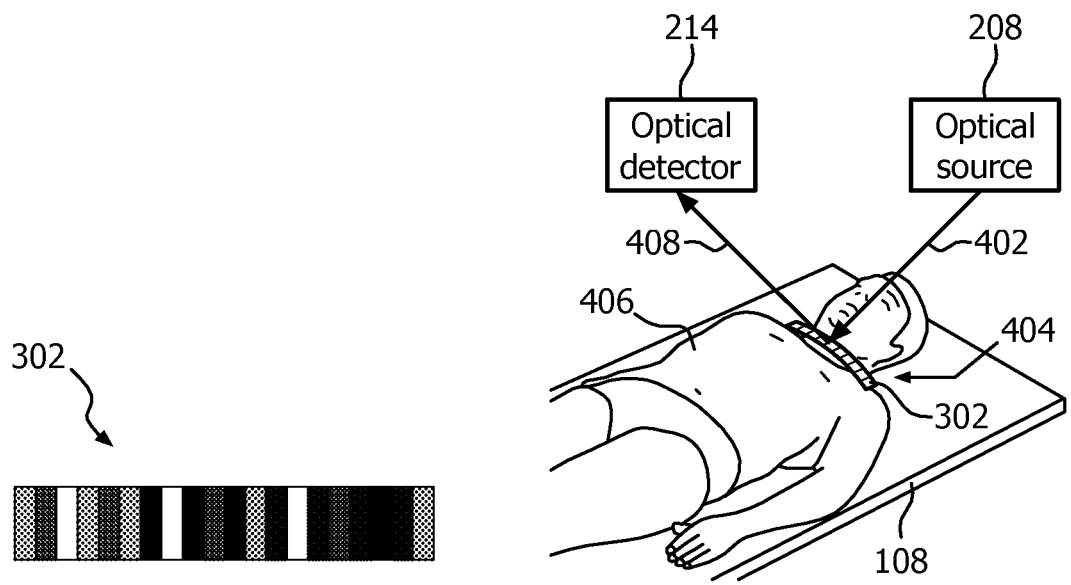
FIG. 3 illustrates an example optical pattern of the subject motion sensing system.
FIG. 4 illustrates an example of projecting the optical signal on a subject and detecting a reflected optical signal.

The particular pattern is determined, for example, based on a pre-determined, but configurable, pattern 212 setting. A suitable pattern, when projected on a subject, will change in shape (which is measurable) in response to deformation or movement of the subject. FIG. 3 shows a non-limiting example of a suitable pattern 302. The pattern 302 includes a plurality of grayscale (as shown) or color bars, each with a predetermined shape. In FIG. 3, the pattern 302 includes a plurality of rectangular bars, each having a same geometry.

In a variation, at least two of the rectangular bars of the plurality of rectangular bars do not have the same geometry. Furthermore, other shapes, including circular, elliptical, triangular, hexagonal, irregular, pictures, etc. are also contemplated herein. In another variation, the pattern may include pulsing the optical signal at a predetermined frequency. In yet another variation, the pattern may include the graphical pattern of FIG. 3 (or other graphical pattern) and the pulsing. Still other patterns are contemplated herein.

Returning to FIG. 2, the receiving portion 204 includes an optical detector 214. The optical detector 214 detects a reflected optical signal, converts the detected reflected optical signal into an electrical signal, and converts the electrical signal into a (digital and/or analog) video signal. For example, the optical detector 214 may include a lens, an imager (e.g., as a CCD, CMOS, etc. sensor), and a video converter. In this instance, the lens focuses the received reflected optical signal onto the imager, which converts the incident optical signal into an electrical signal, and the video converter converts the electrical signal into the video signal. The imager, in one instance, can record in a range of 10 to 50 frames (or higher) per second, such as 20-30 frames per second.

The optical detector 214 is configured to detect electromagnetic radiation corresponding to the wavelength of the projected optical signal. For example, when the optical source 208 is operated to produce an infrared optical signal, the optical detector 214 senses reflected optical signals having a wavelength only in the infrared region of the electromagnetic spectrum, when the optical source 208 is operated to produce a visible light optical signal, the optical detector 214 senses reflected optical signals having a wavelength only in the visible light region of the electromagnetic spectrum, etc. Thus, the optical detector 214 detects a reflection of the projected pattern.

In this example, the motion processor 132 further includes a video memory 216, which stores the video signal, a video processor 218 that processes the stored video signal, and a motion threshold 220. In one instance, the video processor 218 compares a currently generated video signal (with the current pattern) with a stored baseline video signal (for an absolute measurement) and/or stored other video signal (for a relative measurement), and generates a motion signal. The motion signal indicates an amount of pattern deformation between the two compared optical signals. The deformation is indicative of subject motion between the detection times of the two optical signals. The difference signal can be stored in the video memory 216.

In one instance, the motion signal is compared to the motion threshold 220. The motion processor 132, based on a result of the comparison, generates a scan command signal, which is conveyed to the radiation controller 110, which turns radiation emission "on" and/or "off" (e.g., to gate a gate, to acquire data only when subject motion satisfies the threshold, etc.). Alternatively, the motion signal is provided to the reconstructor for a motion-compensated reconstruction and/or to identify a sub-set set of the acquire data with motion characteristics of interest to reconstruct.

As discussed in greater detail below, the optical source 208 and the optical detector 214 are physically arranged with respect to each other so that the optical source 208 projects an optical signal at structure of interest that reflects off the structure of interest and is detected by the optical detector 214. A non-limiting example of this is shown in FIG. 4. In FIG. 4, the optical source 208 projects an optical signal 402 (which includes the pattern 302, in this example) onto a neck region 404 of a patient 406, and the optical detector 214 detects a reflected optical signal 408, which is the projected optical signal reflected off the neck region 404.

In FIG. 4, a single one of the patterns 302 (FIG. 3) is projected along the width of the neck region 404. In this example, the pattern 302 spans at least the entire width of the neck region 404. This allows for detecting motion at a plurality of different points spanning the entire neck region 404. Generally, the number of point and the resolution of the motion detection depends on a size and a number of the individual bars in the pattern 302, with more and narrower bars providing greater resolution relative to less and wider bars. The difference signal may include local deformation information for one or more of the plurality of different points along the neck region 404 and/or global deformation information for multiple points.

In a variation, a plurality of the patterns 302 and/or different patterns is projected as such and are aligned adjacent to each other along the longitudinal axis of the neck region 404. In another variation, the pattern 302 and/or other pattern spans less than the entire width of the neck region 404, e.g., over only a sub-region of interest of the neck region 404. In another variation, a same pattern or different patterns can be projected onto two or more sub-regions of the neck region 404. For example, two patterns can be projected, one to the left and one to the right, with a gap or space in between where no optical signal is projected. In this case, the optical source 214 may include multiple sub-sources.

FIGS. 5, 6, 7 and 8 illustrate non-limiting approaches for projecting the optical signal and detecting the reflected optical signal.

Figure 5:
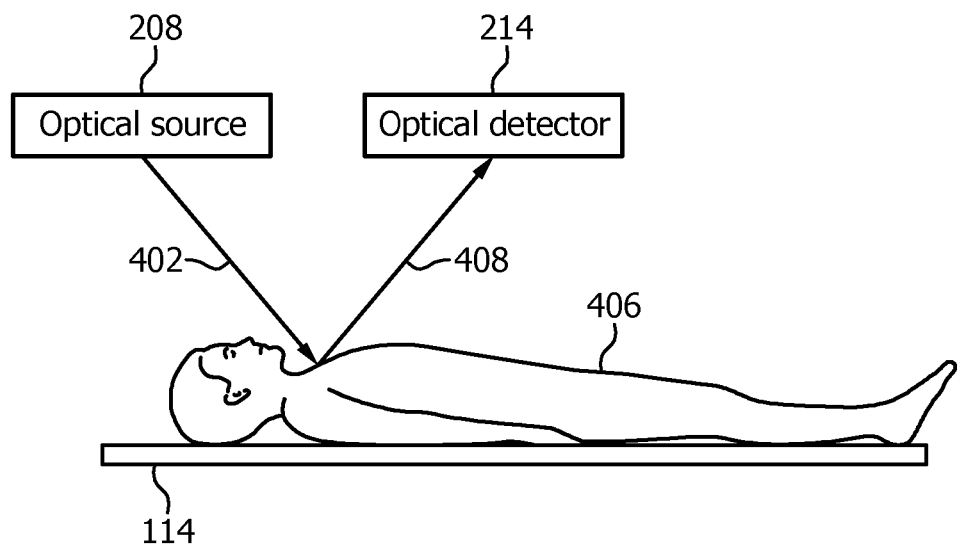
FIG. 5 illustrates an example configuration in which the optical source directly projects the optical signal on the subject and the optical detector directly detects the reflected optical signal.
Figure 6:
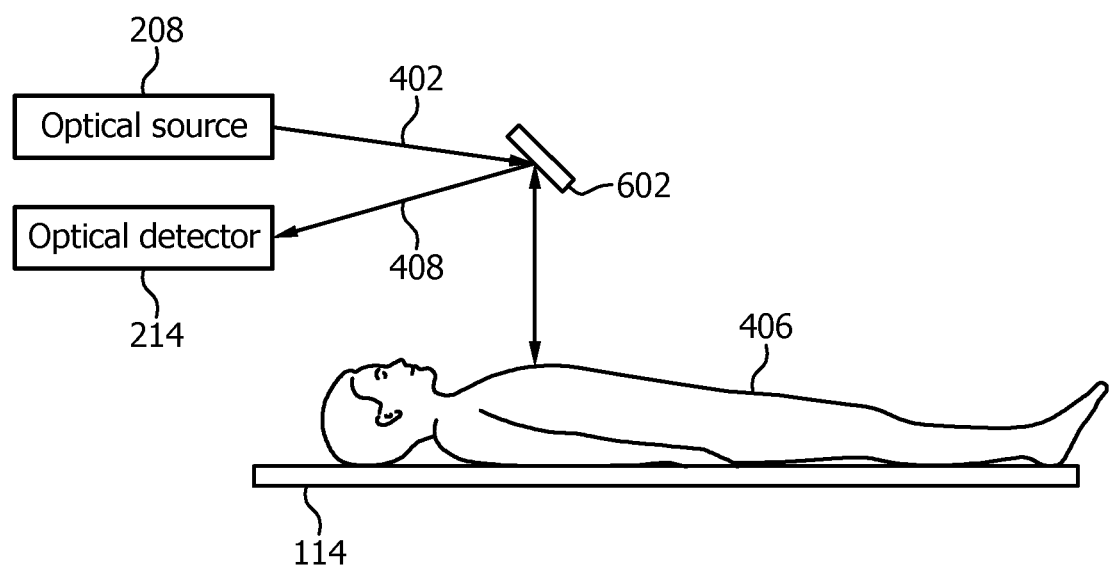
FIG. 6 illustrates an example configuration in which the optical source indirectly projects the optical signal on the subject and the optical detector indirectly detects the reflected optical signal.

In FIG. 5, the optical source 208 projects the optical signal 402 directly onto the patient 406, and the optical detector 214 directly receives the reflected signal 408. In FIG. 6, the optical source 208 projects the optical signal 402 onto a reflector 602, which re-directs or focuses the optical signal 402 onto the patient 406. The reflected signal 408 is received by the reflector 602, which re-directs or focuses the reflected signal 408 at the optical detector 214. In a variation, more than one reflector is used to re-direct or focus signals. This includes using the same and/or different multiple reflectors for the projected signal 402 and/or multiple reflectors for the reflected signal 408.

Figure 7:
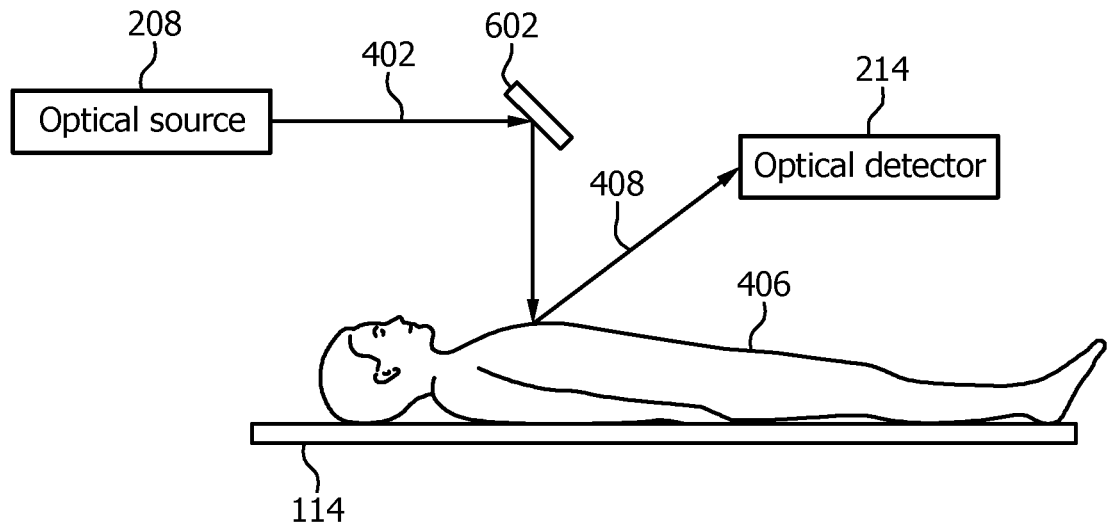
FIG. 7 illustrates an example configuration in which the optical source indirectly projects the optical signal on the subject and the optical detector directly detects the reflected optical signal.
Figure 8:
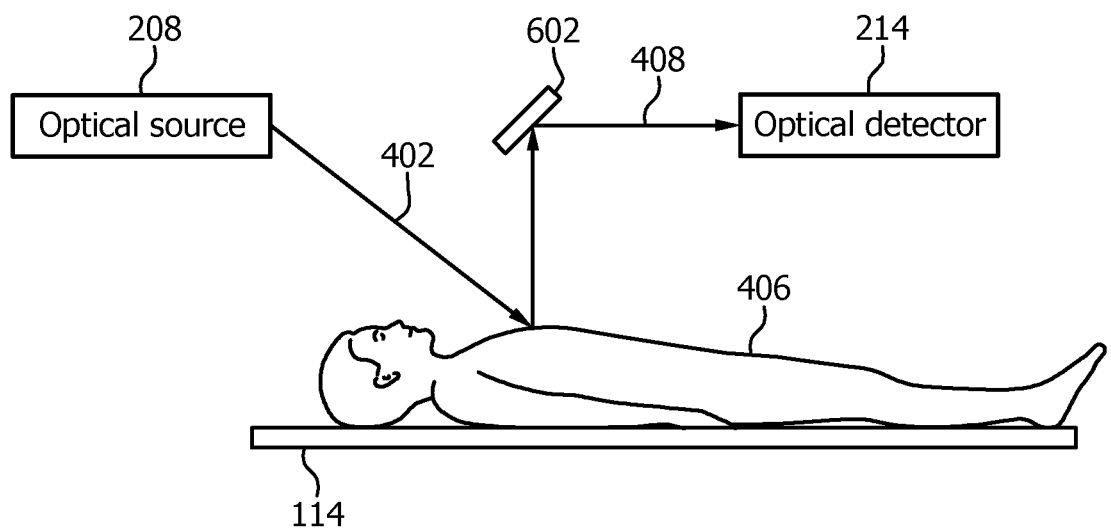
FIG. 8 illustrates an example configuration in which the optical source directly projects the optical signal on the subject and the optical detector indirectly detects the reflected optical signal.

In FIG. 7, similar to FIG. 6, the optical source 208 projects the optical signal 402 onto the reflector 602, which re-directs or focuses the optical signal 402 onto the patient 406, and the optical detector 214, similar to FIG. 5, directly receives the reflected signal 408. Likewise, more than one reflector can be used to re-direct or focus signals. In FIG. 8, similar to FIG. 5, the optical source 208 projects the optical signal 402 directly onto the patient 406, and the optical detector 214, similar to FIG. 6, indirectly receives the reflected signal via the reflector 602. Again, more than one reflector can be used to re-direct or focus signals.

FIGS. 9, 10, 11, and 12 schematically illustrate non-limiting examples of the subject motion sensing system 118 in connection with the rest of the imaging system 100. In these examples, the relative geometry (e.g., shape, size, etc.) of the various components is provided for explanatory purposes and is not limiting.

Figure 9:
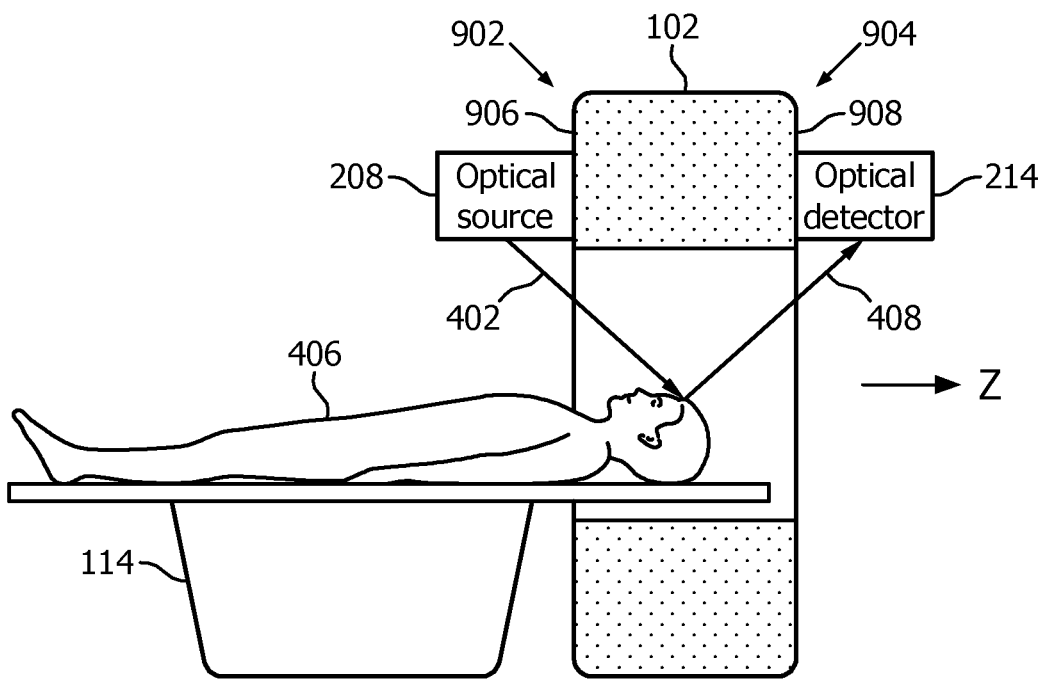
FIG. 9 illustrates an example configuration in which the optical source and the optical detector are affixed to and disposed on opposing sides of the imaging system.

In FIG. 9, the optical source 208 and the optical detector 214 are disposed on opposite sides 902 (front) and 904 (back) of the stationary gantry 102, on opposing outer surfaces 906 and 908 of the sides 902 and 904, along the z-axis direction and above, relative to the floor, the subject support 114. As discussed herein, the optical source 208 and the optical detector are arranged such that the optical source 208 project the optical signal 402 onto the patient 406, and the optical detector 214 detects the reflected optical signal 408.

In the illustrated embodiment, the optical source 208 is on the side 902, which is the side of the imaging system 100 with the subject support 114, and the optical detector 214 is on the back side 904 of the imaging system 100. In a variation, the optical source 208 and the optical detector 214 can be reversed such that they respectively are on the back side 904 and the front side 902 with the subject support 114. In another variation, both the optical source 208 and the optical detector 214 can be on a same side (either 902 or 904) of the stationary gantry 102.

In one instance, the optical source 208 and/or the optical detector 214 are fixedly attached to the stationary gantry 102 via rivets, an adhesive, etc. In another instance, the optical source 208 and/or the optical detector 214 are removably attached to the stationary gantry 102 via screws, bolts, pins, clamps, etc. In yet another instance, the optical source 208 and/or the optical detector 214 are integrated into the sides 902 and 904. This may include being integrated in the system behind the gantry cover (with holes in the cover for transmitting and receiving optical signals) or located outside of the gantry cover.

Figure 10:
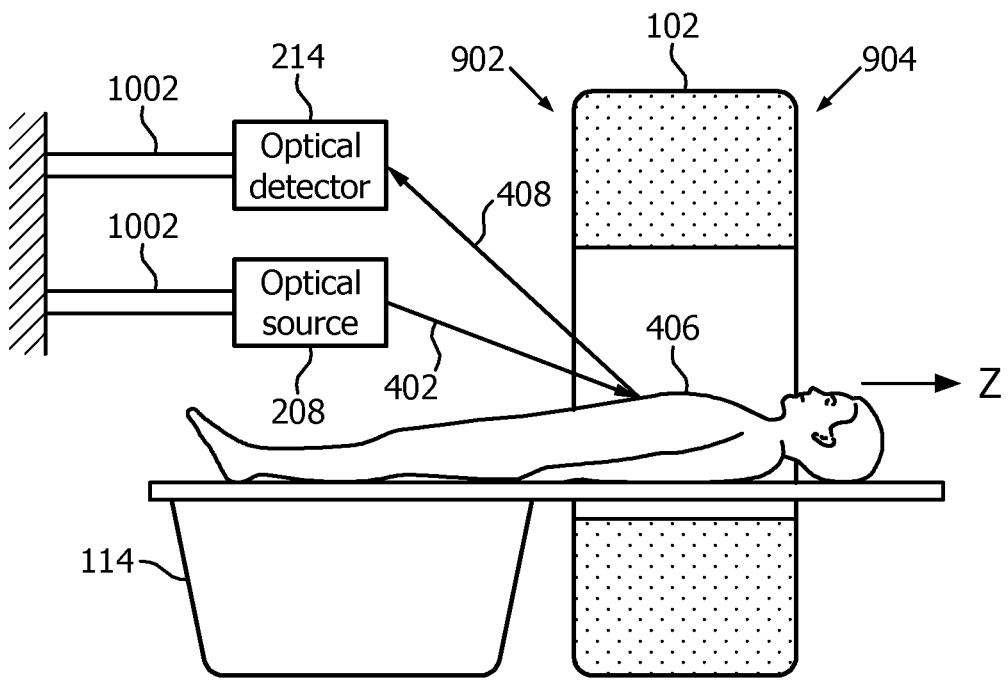
FIG. 10 illustrates an example configuration in which the optical source and the optical detector are affixed to a support external to the imaging system and are located on a same side of the imaging system.

In FIG. 10, both the optical source 208 and the optical detector 214 are supported by a device external to and not (directly or indirectly) part of or attached to the imaging system 100. In this example, at least one support member 1002 (two shown) support the optical source 208 and the optical detector 214. The at least one support member 1002 can be directly affixed to a wall, a ceiling, a mobile stand, and/or other structure. The optical source 208 and the optical detector 214 may be held at fixed positions and/or translatable and/or rotatable. Each at least one support member 1002 may include a sub-set of support members, fixedly and/or moveably attached to one another.

In FIG. 10, similar to FIG. 9, both the optical source 208 and the optical detector 214 are located above the subject support 114. In FIG. 10, both the optical source 208 and the optical detector 214 are located on the side 902. In a variation, one of the optical source 208 or the optical detector 214 can be located on the side 902 and the other of the optical source 208 or the optical detector 214 can be located on side 904. In another variation, both the optical source 208 and the optical detector 214 can be located above on the side 904.

Figure 11:
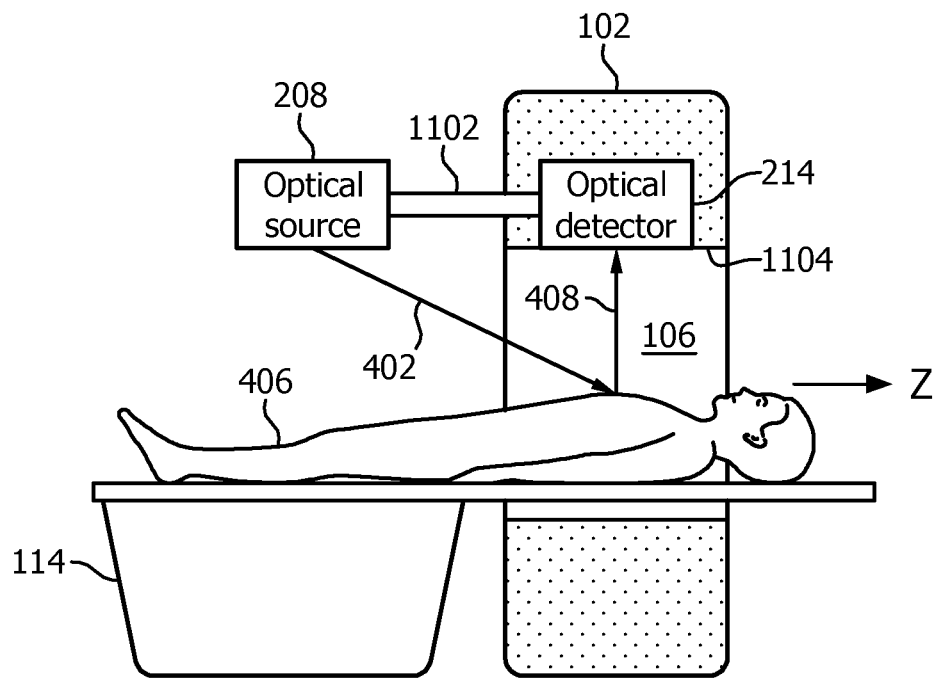
FIG. 11 illustrates an example configuration in which the optical source is indirectly attached to the imaging system through a support and the optical detector is integrated in the imaging system facing the examination region.

In FIG. 11, the optical source 208 is (fixedly or removeably) attached to a support 1102 that is attached to the side 902, and the optical detector 214 is located behind a cover 1104 of the imaging system 100 inside and facing into the examination 106. In a variation, both of the optical source 208 and the optical detector 214 can be attached to at least one of the support 1102 and/or be located behind the cover 1104. In another variation, the optical source 208 and the optical detector 214 are reversed so that the optical detector 214 is (fixedly or removeably) attached to the support 1102, and the optical source 208 is located behind the cover 1104.

Figure 12:
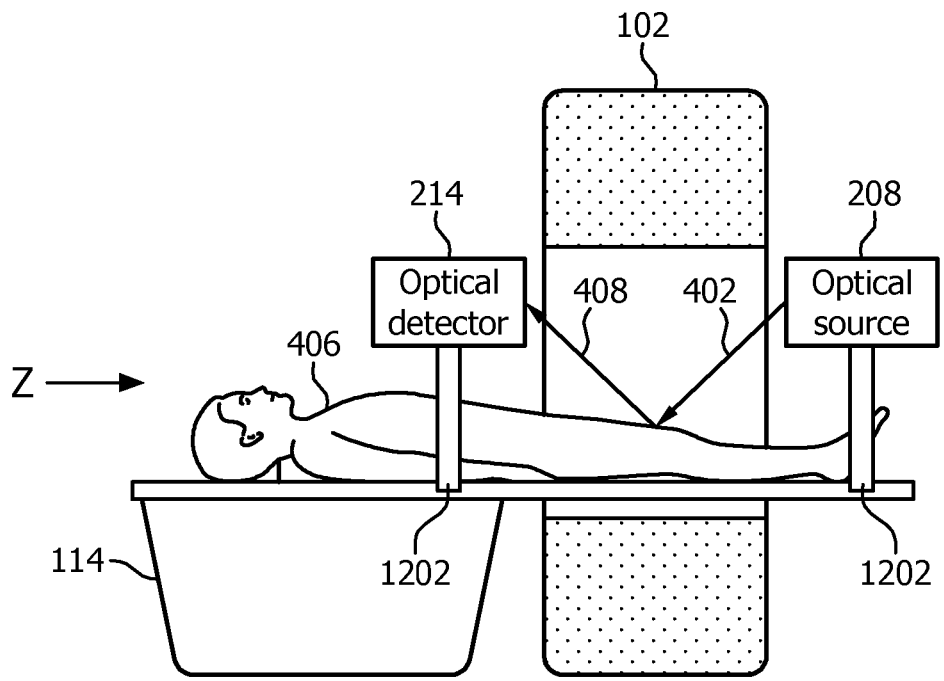
FIG. 12 illustrates an example configuration in which the optical source and the optical detector are affixed to the subject support through a support.

In FIG. 12, the optical source 208 and the optical detector 214 are attached to supports 1202, which are configured to affix to the subject support 114. In this example, the optical detector 214 is on the side 902 and the optical detector 214 is on the back side 904. In a variation, the optical source 208 and the optical detector 214 can be reversed such that they respectively are on the back side 904 end and the front side 902 of the stationary gantry 102.

FIGS. 9-12 show several non-limiting examples of the subject motion sensing system 118. In these examples, the optical source 208 and the optical detector 214 are attached to the imaging system and/or a device external to the imaging. In these examples, neither the optical source 208 nor the optical detector 214 contacts the subject. In another embodiment, at least one component (e.g., the optical source 208, the optical detector 214, etc.) of the subject motion sensing system 118 contacts the subject.

For helical scanning, the speed of the subject support 114 can be used to distinguish between deformation of the pattern due to the landscape or contour of the subject and the involuntary and/or voluntary motion discussed herein. This can be done using a pre-scan (e.g., scout), optical information obtained by the subject motion sensing system 118 over the subject, a previous scan of the subject, an anatomical model, and/or other information. The optical information can be obtained anytime from the time the subject is placed on the subject support 114 until the subject is unloaded from the subject support 114.

Figure 13:
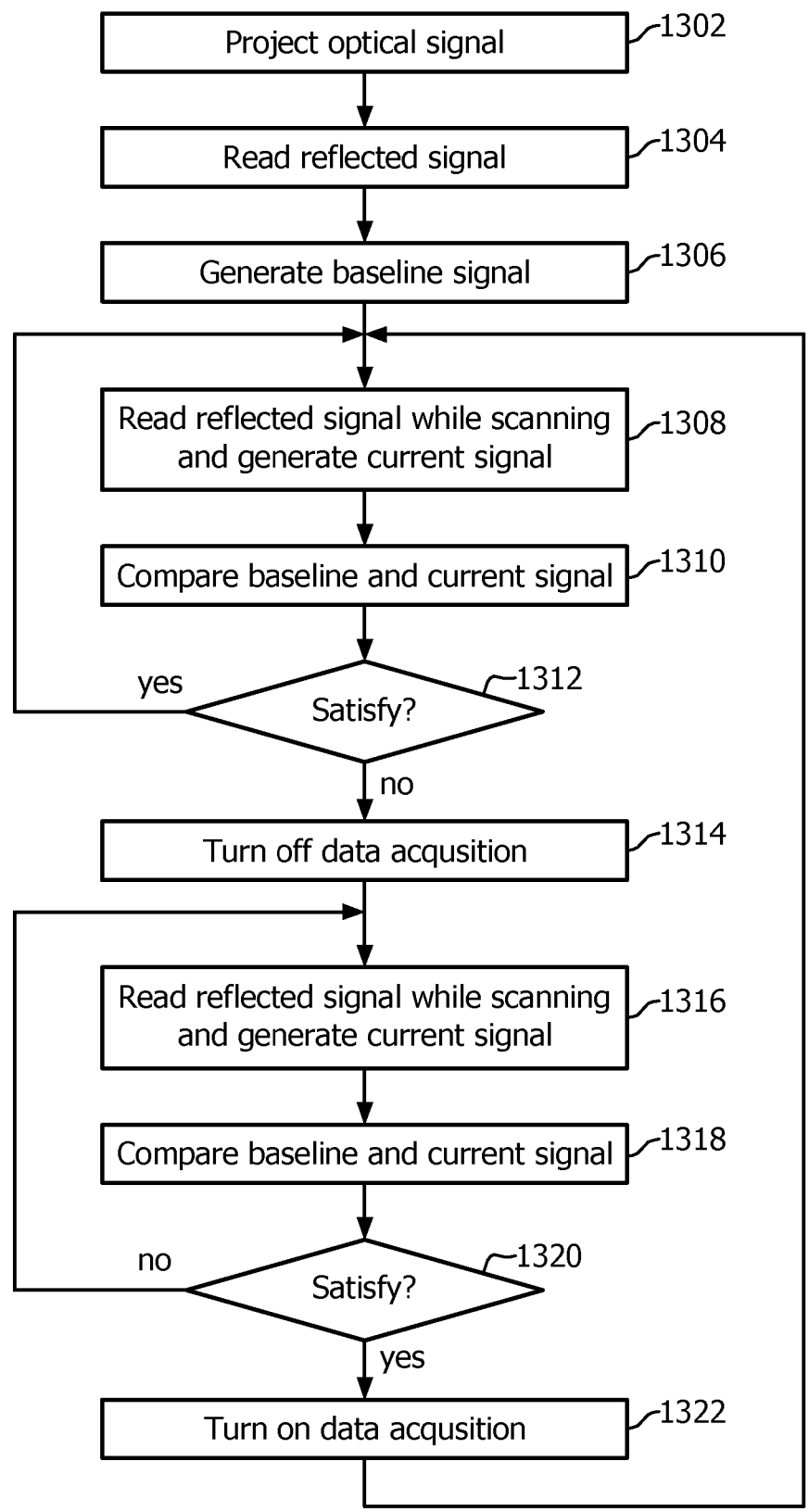
FIG. 13 illustrates an example method for temporarily pausing or turning off data acquisition only when subject motion is greater than a pre-determined threshold and resuming or turning data acquisition back on when subject motion is less than the pre-determined threshold.

FIG. 13 illustrates an example method for temporarily pausing or turning off data acquisition only when subject motion is greater than a pre-determined threshold and resuming or turning data acquisition back on when subject motion is less than the pre-determined threshold.

It is to be appreciated that the ordering of the acts in the methods described herein is not limiting. As such, other orderings are contemplated herein. In addition, one or more acts may be omitted and/or one or more additional acts may be included.

At 1302, an optical source projects an optical signal, having a known pattern and wavelength, onto a portion of a subject in an examination region of an imaging system.

At 1304, an optical detector detects a reflection signal, which is generated in response to the optical signal reflecting off the portion of the subject in the examination region. For this, the optical detector may detect one or more frames or cycles of data. This signal can be acquired prior to or concurrently with scanning.

At 1306, the detected reflected signal is converted to a baseline video signal.

At 1308, while scanning of the portion of a subject in an examination region of an imaging signal, the optical detector detects the reflection signal and converts the detected reflected signal to a current video signal.

At 1310, the current video signal and the baseline video signal are compared to determine a difference value, which represents a difference between the patterns at two points in time, which is indicative of a physical subject motion there between.

At 1312, the difference value is compared to a predetermined threshold value, and it is determined whether the difference value satisfies the predetermined threshold value.

In response to the difference value satisfying the predetermined threshold value, acts 1308-1312 are repeated.

At 1314, in response to the difference value not satisfying the predetermined threshold value, data acquisition and hence radiation emission is turned off. Generally, the threshold value is set at a level where the motion introduces motion artifact which is greater than a predetermined amount of artifact deemed tolerable by the clinician, the imaging facility, etc.

At 1316, the optical detector continues to detect the reflection signal and generate current video signal.

At 1318, the current video signal and the video baseline signal are compared to determine a difference value, as discussed in act 1308.

At 1320, the difference value is compared to a predetermined threshold value, as discussed in act 1310.

In response to the difference value not satisfying the predetermined threshold value, acts 1316-1318 are repeated.

At 1322, in response to the difference value satisfying the predetermined threshold value, data acquisition and hence radiation emission is turned on, and acts 1308-1312 are repeated.

Of course, where the scanner is not a CT scanner and is a PET, SPECT, MRI, and/or scanner that does not emit radiation or does not emit x-ray radiation, turning data acquisition on and off does not turn x-ray radiation on and off.

The above may be implemented by way of computer readable instructions, encoded or embedded on computer readable storage medium (which excludes transitory medium), which, when executed by a computer processor(s), cause the processor(s) to carry out the described acts. Additionally or alternatively, at least one of the computer readable instructions is carried by a signal, carrier wave or other transitory medium.

Figure 14:
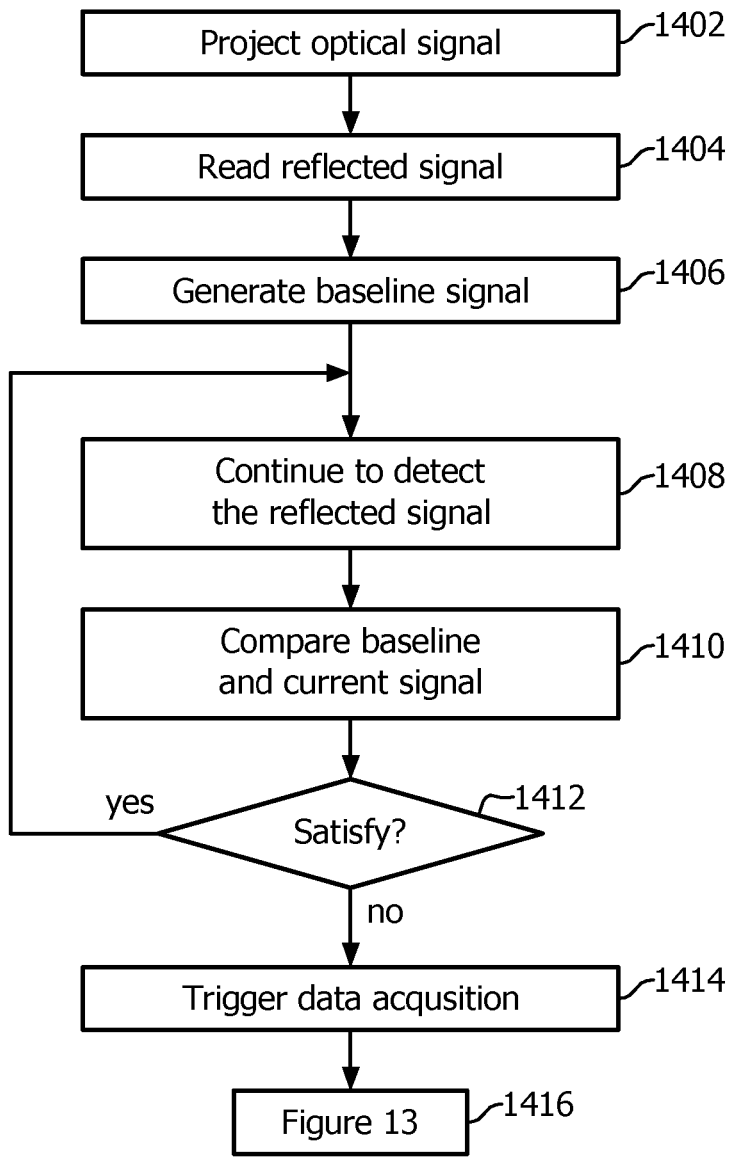
FIG. 14 illustrates an example method for triggering data acquisition based on motion.

FIG. 14 illustrates an example method for triggering data acquisition based on motion.

It is to be appreciated that the ordering of the acts in the methods described herein is not limiting. As such, other orderings are contemplated herein. In addition, one or more acts may be omitted and/or one or more additional acts may be included.

At 1402, an optical source projects an optical signal, with a known pattern and wavelength, onto a portion of a subject in an examination region of an imaging system.

At 1404, an optical detector detects a reflection signal, which is generated in response to the optical signal reflecting off the portion of the subject in the examination region.

At 1406, the detected reflected signal is converted to a baseline video signal.

At 1408, the optical detector continues to detect the reflection signal.

At 1410, the current video signal and the baseline video signal are compared to determine a difference value, which represents a difference between the patterns at two points in time, which is indicative of a physical subject motion there between.

At 1412, the difference value is compared to a predetermined threshold value, and it is determined whether the difference value satisfies the predetermined threshold value.

In response to the difference value not satisfying the predetermined threshold value, acts 1408-1410 are repeated.

At 1414, in response to the difference value satisfying the predetermined threshold value, data acquisition is triggered.

At 1416, the method of FIG. 13 is executed. In a variation, the method of FIG. 13 is not executed.

The above may be implemented by way of computer readable instructions, encoded or embedded on computer readable storage medium (which excludes transitory medium), which, when executed by a computer processor(s), cause the processor(s) to carry out the described acts. Additionally or alternatively, at least one of the computer readable instructions is carried by a signal, carrier wave or other transitory medium.

Figure 15:
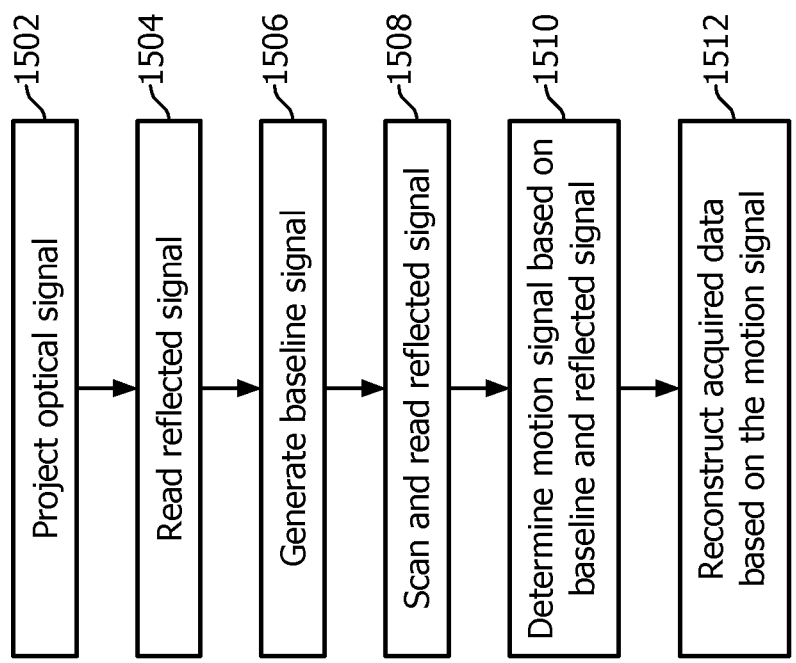
FIG. 15 illustrates an example method for generating a motion compensation signal and using the motion compensation signal during reconstruction to motion-compensate the acquired data.

FIG. 15 illustrates an example method for generating a motion compensation signal and using the motion compensation signal during reconstruction to motion-compensate the acquired data.

It is to be appreciated that the ordering of the acts in the methods described herein is not limiting. As such, other orderings are contemplated herein. In addition, one or more acts may be omitted and/or one or more additional acts may be included.

At 1502, an optical source projects an optical signal, with a known pattern and wavelength, onto a portion of a subject in an examination region of an imaging system.

At 1504, prior to scanning the portion of the subject in the examination region, an optical detector detects a reflection signal, which is generated in response to the optical signal reflecting off the portion of the subject in the examination region.

At 1506, the detected reflected signal is converted to a baseline video signal.

At 1508, the optical detector continues to detect the reflection signal while the scan is performed.

At 1510, a motion signal is determined based on the baseline video signal and the reflected video signal detected during the scan.

At 1512, the acquired data is reconstructed using the motion signal (and/or the baseline video signal and/or the current video signal) to motion correct the data.

The above may be implemented by way of computer readable instructions, encoded or embedded on computer readable storage medium (which excludes transitory medium), which, when executed by a computer processor(s), cause the processor(s) to carry out the described acts. Additionally or alternatively, at least one of the computer readable instructions is carried by a signal, carrier wave or other transitory medium.

Figure 16:
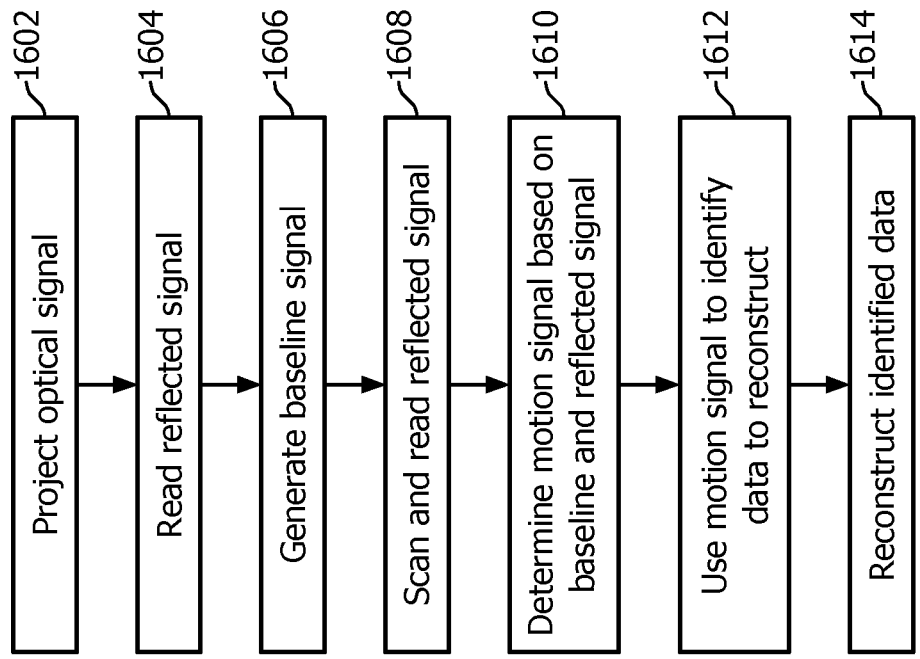
FIG. 16 illustrates an example method identifying a sub-set of data from a scan to reconstruct based on motion.

FIG. 16 illustrates an example method identifying a sub-set of data from a scan to reconstruct based on motion.

It is to be appreciated that the ordering of the acts in the methods described herein is not limiting. As such, other orderings are contemplated herein. In addition, one or more acts may be omitted and/or one or more additional acts may be included.

At 1602, an optical source projects an optical signal, with a known pattern and wavelength, onto a portion of a subject in an examination region of an imaging system.

At 1604, prior to scanning the portion of the subject in the examination region, an optical detector detects a reflection signal, which is generated in response to the optical signal reflecting off the portion of the subject in the examination region.

At 1606, the detected reflected signal is converted to a baseline video signal.

At 1608, the optical detector continues to detect the reflection signal while the scan is performed.

At 1610, a motion signal is determined based on the baseline video signal and the reflected video signal detected during the scan.

At 1612, a sub-set of the acquired data, which corresponds to data acquired is the presence of less than a threshold amount of motion, is identified based on the motion signal (and/or the baseline video signal and/or the current video signal).

At 1614, only the identified acquired data is reconstructed.

The above may be implemented by way of computer readable instructions, encoded or embedded on computer readable storage medium (which excludes transitory medium), which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   a subject support configured to support a subject in an examination region;
   an optical source configured to project an optical pattern on a portion of the subject in the examination region;
   a detector configured to detect first and second reflected optical patterns reflected off the portion of the subject in response to the projected optical pattern and generate first and second signals based, respectively, on the first and second reflected optical patterns;
   at least one processor configured to detect a difference between the first and the second signals and generate a motion data based on the difference, wherein the projected optical pattern is created to have the motion data generated at a plurality of points along the portion of the subject; and
   a console configured to control at least one of data acquisition and reconstruction based on the motion data.

2. The imaging system of claim 1, wherein the optical source generates an optical signal based on a wavelength setting such that the optical signal has a wavelength in at least one of an infrared band, a visible band, and ultraviolet band of an electromagnetic spectrum, and the optical detector is configured to detect in at least one of the bands of the optical signal.

3. The imaging system of claim 1, wherein the optical source generates the optical pattern based on a pattern setting, and the optical pattern changes in response to a motion of the subject, and wherein the change is related to a physical deformation of the subject caused by the motion.

4. The imaging system of claim 1, further comprising:
   a memory configured to store at least the first and second signals.

5. The imaging system of claim 1, wherein the motion data includes at least one of a plurality of local motion signals spanning the projected optical pattern and a global motion signal for the projected optical pattern.

6. The imaging system of claim 1, wherein the at least one processor makes a comparison between the motion data and a predetermined motion threshold and generates a command signal based on the comparison.

7. The imaging system of claim 6, further comprising:
   a source controller, wherein the console conveys a command signal to the source controller, and wherein the source controller, in response to the command signal indicating the motion data exceeds the threshold, changes a state of signal transmission.

8. The imaging system of claim 7, wherein the source controller turns the signal transmission off by at least one of: moving a filter in a path of the signal transmission, setting a grid voltage of a switching grid to inhibit electrons to flow from a cathode to an anode of the source, and removing a power to the optical source.

9. The imaging system of claim 8, wherein the console conveys the command signal to the source controller, and the source controller, in response to the command signal indicating the motion data does not exceed the threshold, turns the signal transmission on by at least one of: moving the filter out of the path, changing the grid voltage to allow electrons to flow from the cathode to the anode, suppling the power to the optical source.

10. The imaging system of claim 7, wherein the source controller turns the signal transmission on by suppling power to the optical source.

11. The imaging system of claim 1, wherein the at least one processor is further configured to reconstruct an output of the detector to generate image data indicative of the examination region, wherein the console is further configured to provide the motion data to the at least one processor in order to correct for motion artifacts in the output of the detector.

* * * * *